United States Patent
Tjioe

(12) 
(10) Patent No.: US 7,361,217 B2
(45) Date of Patent: Apr. 22, 2008

(54) METHOD FOR CRYSTALLISING A MELAMINE MELT

(75) Inventor: Tjay Tjien M. Tjioe, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 232 days.

(21) Appl. No.: 10/541,796

(22) PCT Filed: Jan. 28, 2004

(86) PCT No.: PCT/NL2004/000062

§ 371 (c)(1),
(2), (4) Date: Jul. 11, 2005

(87) PCT Pub. No.: WO2004/074265

PCT Pub. Date: Sep. 2, 2004

(65) Prior Publication Data

US 2006/0112872 A1      Jun. 1, 2006

(30) Foreign Application Priority Data

Feb. 24, 2003   (NL) .................................. 1022764

(51) Int. Cl.
*C30B 28/04*   (2006.01)
(52) U.S. Cl. ...................... 117/5; 117/2; 117/3; 117/4; 117/7
(58) Field of Classification Search .................. 117/2, 117/3, 4, 7, 5
See application file for complete search history.

(56) References Cited

U.S. PATENT DOCUMENTS 3,637,686 A * 1/1972 Kokubo et al. ............. 544/203
5,384,440 A   1/1995 Wnuk et al.
5,514,796 A   5/1996 Best
6,706,856 B2 * 3/2004 Aarts et al. .................. 528/424
7,176,309 B2 * 2/2007 Schroder et al. ............ 544/203

FOREIGN PATENT DOCUMENTS

| WO | 96/20933 A1 | 7/1996 |
| WO | 99/46251 | 9/1999 |
| WO | 00/53587 | 9/2000 |
| WO | 01/72722 | 10/2001 |
| WO | 01/727222 | 10/2001 |

OTHER PUBLICATIONS

International Search Report.

* cited by examiner

*Primary Examiner*—Felisa Hiteshew
(74) *Attorney, Agent, or Firm*—Nixon & Vanderhye P.C.

(57) ABSTRACT

Method for crystallizing a melamine melt to form melamine particles with a $D_{90}$ of at most 2 mm by cooling a melamine melt to below the crystallization temperature of the melamine, comprising the formation of a suspension of melamine particles in the cooling medium by spraying the melamine melt with at most 10 wt % of $CO_2$ relative to the sprayed quantity of melamine melt in a space in which a layer of a liquid cooling medium is present that has a temperature below the crystallization temperature of the melamine and under cooling conditions at which at least 50 wt % of the sprayed melamine melt directly turns into suspended melamine particles. Method for the production of melamine from urea in a preferably continuous, high-pressure process, with application of the present method for the crystallization.

9 Claims, No Drawings

METHOD FOR CRYSTALLISING A MELAMINE MELT

This application is a 371, U.S. National phase of international application PCT/NL04/00062 filed 28 Jan. 2004 which designated the U.S. and claims benefit of NL 1022764, dated 24 Feb. 2003, the entire content of which is hereby incorporated by reference.

The invention relates to a method for crystallising a melamine melt to form melamine particles with a $D_{90}$ of at most 2 mm by cooling a melamine melt to below the crystallisation temperature of the melamine.

Melamine is generally manufactured from urea using a number of different known processes. Processes are known which are operated at high pressure and processes which are operated at lower pressures. In the case of the high-pressure processes in the first instance liquid melamine is formed, in other processes the melamine becomes available in gaseous form. The invention is applicable in particular to the liquid melamine melt from processes operated as a rule at high pressure.

The melamine melt thus obtained is usually worked up afterwards to form melamine powder as the most current form in which melamine is processed further. An essential process step here is always crystallising the melamine melt by cooling to below the crystallisation temperature of the melamine in order to obtain solid melamine in particle form. This cooling takes place in known processes by for example contacting the melamine, which usually becomes available from the reactor in the form of a mixture of liquid melamine with gaseous components such as $CO_2$, $NH_3$ and gaseous melamine, with an aqueous liquid, which results in the formation of a slurry or solution. From this slurry, melamine is then separated; the melamine is purified and recrystallised in further process steps to form the melamine final product. A further recrystalisation step is necessary, because the product obtained in slurry form fails to meet the desired specifications in relation to physical and/or chemical properties of the final product. The $D_{90}$ of a particle-shaped product is understood to be that value of the particle size at which 90 wt % of the product has a particle size smaller than this value.

From U.S. Pat. No. 5,514,796 it is known to cool a melamine melt after separation of the said gaseous constituents with liquid ammonia, whereby the ammonia evaporates. A disadvantage of this method is that the physical properties such as particle porosity, particle size distribution and dissolution rate are difficult to control while preserving the desired chemical purity. Another disadvantage is the formation of melamine dust that must be separated from the gases.

From WO 01/72722 A1 it is known to add a melamine melt to a crystallisation section containing liquid ammonia, with the melamine melt cooling to below the crystallisation point so that a suspension of melamine crystals is formed in liquid ammonia. By gravity the melamine falls dropwise through a sieve plate into the liquid ammonia. Cooling in a liquid cooling medium offers per se advantages over cooling in the gas phase with an evaporating medium, because no melamine dust is formed which must be separated from the gases. Furthermore for cooling a melamine melt in a liquid cooling medium significantly less space is necessary than for cooling by evaporation of a cooling medium.

This known method has the disadvantage that the physical properties of the obtained crystallised melamine are difficult to influence, while depending on the application of the melamine different physical properties, such as particle porosity, particle size distribution and dissolution rate can be desirable.

The object of the invention is to provide a method for the preparation of melamine particles by cooling a melamine melt which makes it possible to control better than with the known method the physical properties such as particle porosity, particle size and particle size distribution and dissolution rate of the obtained melamine.

This object is achieved according to the invention because the method comprises forming a suspension of melamine particles in the cooling medium by spraying the melamine melt with at most 10 wt % of $CO_2$ relative to the sprayed quantity of melamine melt in a space wherein a layer of a liquid cooling medium is present that has a temperature below the crystallisation temperature of the melamine and under cooling conditions at which at least 50 wt % of the sprayed melamine melt turns into suspended melamine particles.

Preferably the $CO_2$ content is lower than 10 wt %, more preferably lower than 5 wt % and most preferably at most 2 wt %. A low $CO_2$ content is preferable because the presence of $CO_2$ influences on the one hand the chemical purity of the melamine particles themselves, but may also bring about the formation of other crystals, for example of ammonium carbamate, which may hinder the separation of the melamine later in the process. Also, the cooling medium should preferably contain less than 10 wt % of $CO_2$ and more preferably less than 5 wt % and most preferably at most 2 wt %. The same preferences apply to the total of the $CO_2$ coming from the melt and the cooling medium. For a very high purity it is advantageous if the $CO_2$ content is low in both the melt and in the cooling medium and the total remains within the given limits.

With the method according to the invention it has become possible through a suitable choice of the spraying equipment and the spraying conditions such as pressure drop, outflow velocity, outlet, to control the physical properties whilst preserving the desired chemical purity. It was found that the form in which and the circumstances under which the melamine melt is brought into contact with the liquid cooling medium determines the physical properties of the cooled melamine particles and not the presence of the microcrystals, mentioned as a determining factor in WO 01/72722 A1. Furthermore with the method according to the invention melamine can be obtained in a wide range of physical properties with a purity sufficient for most applications. A further advantage of the method according to the invention is that it yields melamine with the desired physical and chemical properties in one step without an additional recrystallisation step being necessary.

The melamine melt to which the method according to the invention is applicable is in essence any melamine melt, both a melt directly obtained from a process in which melamine is formed in a molten state and a melt that has been formed by melting melamine from the solid state. In the first case the method can be applied directly to the reaction mixture obtained from the process, provided that so so much $CO_2$ is removed from it that the remaining quantity of $CO_2$ that is present with the melamine melt or dissolved in it amounts to at most 10 wt % and preferably at most 5 and more preferably at most 2 wt % relative to the sprayed quantity of molten melamine. If desired the melamine melt can before the spraying be separated from a larger quantity of $CO_2$ and even from all gaseous by-products from the reaction mixture. The method according to the invention can also be applied to a thus separated melt that afterwards has undergone one or more further treatments, such as an ageing step and/or a stripping step and/or a precooling step of the melt, with the melt remaining liquid however, to reduce the quantity of by-products further. During the spraying, however, the quantity of $CO_2$ relative to the sprayed quantity of molten melamine must always remain within the aforesaid limits. Any gaseous constituents added to the space in which the cooling takes place are removed from it, for example together with evaporated coolant or other superfluous gaseous constituents.

A further advantage of the method according to the invention is that the cooling can also take place at an elevated pressure, so that a melamine melt from high-pressure processes can also be cooled without further pressure adaptation.

Processes in which a melamine melt is formed are known per se. These comprise as a rule the conversion of urea into melamine at pressures between 4 and 25 MPa and at temperatures between 330 and 430° C. The reaction product obtained contains liquid melamine, $CO_2$ and $NH_3$ and is as a rule transferred to a separator which is preferably kept at almost the same pressure as the reactor. In this separator the reactor product is separated into a gaseous flow and a liquid flow. The gaseous flow contains $CO_2$ and $NH_3$ off-gases and also melamine vapour. The liquid flow consists principally of liquid melamine. The liquid melamine is then subjected to a cooling step. The method according to the invention now provides a new and advantageous method for carrying out this cooling step.

In the method according to the invention the melamine melt, preferably separated from at least a part of the gaseous ingredients present in the original reactor product, in particular from the $CO_2$, so that the quantity thereof remains within the above-mentioned limits, is sprayed in a liquid cooling medium, with the solidification taking place mainly in the liquid cooling medium. The temperature at which the melamine melt is sprayed at the prevailing pressure in the space from which the melt is sprayed preferably lies between 1 and 50° C. above the crystallisation temperature of the melamine at the prevailing pressure and more preferably between 1 and 30° C. above it and most preferably between 2 and 20° C. above it. To reach the desired temperature the melt can, if necessary, prior to the spraying be cooled down or heated up from the temperature at which the melt becomes available. To counter the formation of unwanted by-products of the melamine the melamine melt is kept under pressure, preferably under ammonia pressure. This pressure lies between 4 and 25 MPa and preferably between 8 and 18 MPa.

The melt can be sprayed per se but it is also possible to spray the melt as a two-phase mixture together with a gas. As the gas an inert gas can be applied but, to limit the number of different components to be separated from each other again later in the process, ammonia is preferably applied as the gas or the substance applied as a cooling medium in gas form. The application of a gas has been found to constitute an extra parameter in controlling the physical properties such as particle porosity and particle size. The volume fraction of gas can vary over a large area, for example from 0 to 95, preferably 5 to 80 volume % of the mixture of melamine melt and gas. For technical and economic reasons it will usually be chosen to take a quantity of gas that is not larger than is necessary to obtain the desired particle size in the spraying process. The gas is fed to the melt in such a way that a two-phase mixture is formed. This may be done for example by feeding the gas under the desired pressure to the melt in a feed line to the spraying facilities with which the melt is sprayed.

For spraying of the melt, suitable equipment known per se for the spraying of liquid substances can be applied. Spraying can take place using one or more spray nozzles, each provided with one or more spray openings. By suitably choosing for example the pressure drop between the space out of which the melt is sprayed and the space into which it is sprayed, the quantity of gas that is optionally co-sprayed, the size and the shape of the openings through which the spraying takes place and the position of the openings relative to the liquid level of the cooling medium, the physical properties of the resulting melamine particles can be controlled. The velocity of the sprayed melamine melt when exiting from the spray opening is preferably at least 2 m/s, more preferably at least 5 m/s and most preferably at least 10 m/s. These velocities are significantly higher than the gravity-induced outflow velocity as reached in WO 01/72722 A1. The upper limit of the outflow velocity in a given installation is determined by the permissible pressure drop in the spraying step and the mechanical construction of the spray system. The pressure drop in the spraying step generally amounts to more than 5 kPa and preferably more than 25 kPa, and more preferably between 0.1 MPa and 20 MPa. With higher pressure drops the probability of blockage of the sprayer is smaller. On the other hand with higher pressure drops finer particles are formed with the same sprayer opening, so that the separation of the slurry becomes more difficult. It was found that the average particle size can be set over an ample range, given an adequate choice of the pressure drop, the quantity of gas that is co-sprayed and the construction of the spray system.

The spray openings can be situated above the liquid surface of the cooling medium. The sprayed melt then moves down and then comes in contact with the liquid cooling medium. The spray openings can also be situated under that surface, so that the sprayed melt comes directly in contact with the cooling medium. An advantage of this last embodiment is that the cooling takes place faster. It is then advisable to take measures that prevent a situation where the melamine melt already solidifies in the nozzle and would block the spray openings. This can be prevented for example by thermally insulating or heating the spray nozzle. When spraying the melamine melt above the liquid surface the melamine can already be cooled to some extent by also spraying cooling medium above the cooling surface. The cooling of the melamine melt before it comes in contact with the layer of cooling medium should however be so limited that the melamine is still more than 25%, preferably more than 50% and most preferably more than 75% liquid when it comes in contact with the layer of cooling medium and further solidifies therein.

Through a suitable choice of the above-mentioned parameters which determine the spraying process the spraying process is further preferably set in such a way that particles with a $D_{90}$ smaller than 2 mm, more preferably smaller than 1 mm and most preferably smaller than 0.5 are obtained. This can be achieved by a suitable choice of the combination of outflow velocity and size and/or shape of outlets. The standardised outlet of the sprayer preferably lies between 6 and 100 $mm^2$, more preferably between 8 and 80 $mm^2$ at a sprayer capacity of 1 kg/s melamine melt flow. The standardised outlet of the sprayer is understood to be: A/M, where A=the smallest flow opening in the sprayer (in $mm^2$) for the melamine melt;

M=the melamine melt flow (in kg/s).

If the melamine melt flow has been combined with a gas flow M only refers to the liquid flow. If the $D_{90}$ remains above 30 μm, separation of the melamine particles from the cooling medium with a sufficiently high efficiency has been found possible. A very suitable range for the $D_{90}$ is between 50 and 500 μm.

The cooling medium is present in a vessel in which an elevated pressure can be maintained. Preferably the pressure in the vessel lies between 0.1 MPa and 20 MPa so that melamine melts coming from the known processes that yield a melamine melt can be sprayed in said vessel at the pressure at which they become available from those processes. More preferably the pressure lies between 1 and 18 MPa. The advantage of this method is that it is possible to opt for optimisation of the physical or chemical properties. If high demands are placed on the physical properties a higher pressure drop in the spraying step can be chosen, which may imply loss in terms of the chemical purity, depending on the sprayer properties. A higher pressure drop enables influencing the porosity over a larger range.

As a cooling medium in principle any substance is suitable that is liquid in at least a part of the temperature range between 20° C. and 200° C. at the prevailing pressure in the cooling vessel. As a cooling medium water and ammonia can be used and preferably a mixture of ammonia and water is applied. In that case the amount of ammonia in the water/ammonia mixture that is applied as the liquid cooling medium should be at least 10 wt %, more preferably at least 20 wt %, still more preferably at least 50 wt % and even 75 wt % and most preferably at least 90 wt %. At lower water contents a larger part of the melamine melt can be obtained directly as a solid without further cooling, because the solubility of the melamine is lower. Furthermore ammonia is a substance which generally occurs in almost all steps of the melamine production and working up process, so that by using ammonia as a cooling medium no new substance extraneous to the process is introduced that must be separated again separately later. Further, the pressure in the cooling vessel may be chosen much lower than before the sprayer, because ammonia can be kept liquid over a large range, so that the physical properties of the formed melamine particles can be influenced over a wide range.

The temperature of the cooling medium is lower than the crystallisation temperature of the melamine in the melt and preferably at least 100° C. lower to achieve rapid cooling, before the effect of the turbulence in the cooling medium, which effect is generated in it by the spraying of the melt, has disappeared. The product is preferably cooled to a temperature below 200° C. and more preferably to below 150° C.

Due to supply of the melamine melt the cooling medium will heat up, so that heat must be removed from it in order to maintain the desired temperature of the cooling medium. Heat can be removed for example by choosing the temperature of the cooling medium close to its boiling temperature, so that a considerable degree of evaporation of the cooling medium occurs and consequently heat is extracted from it. The evaporated medium is then removed from the cooling vessel and upon condensation it may be returned to the vessel as a cooling medium, if desired supplemented with fresh cooling medium. Another way to remove heat from the cooling medium is for example removing a part of the liquid cooling medium to outside the vessel, cooling it there and returning the cooled medium to the vessel, again if desired supplemented with or replaced in whole or in part by fresh cooling medium. This method of cooling can be chosen when the temperature of the cooling medium is significantly lower than the boiling temperature of the cooling medium, because under that circumstance the capacity of cooling by evaporation is insufficient.

Due to the contact with the cooling medium the sprayed melamine melt turns into the solid melamine particles, so that a suspension of solid melamine in the cooling medium is formed. The quantity of melamine melt added per time unit is chosen, in combination with the heat-removing capacity of the system with which the cooling medium is cooled, such that the desired rapid cooling remains guaranteed. In addition the quantity of the melamine supplied to the cooling medium should be chosen so large that the concentration of the melamine remains well above the saturation point in the used cooling medium, so that the desired suspension of melamine particles is obtained and not only a solution of melamine in the cooling medium. The cooling conditions are set such that the weight fraction of the melamine melt that is obtained directly in this cooling stage as a solid in the form of suspended melamine particles is at least 50 wt %, more preferably is larger than 75 wt % and most preferably is larger than 90 wt % relative to the quantity of melamine melt supplied to the cooling medium by spraying. A melamine is thus obtained of which at least one half consists of particles with the desired properties, so that these are sufficiently reflected in the further processing of the finally obtained melamine, even if the melamine particles are mixed with melamine particles that have been recovered for example in a recirculation step from the melamine dissolved in the cooling medium.

In a continuous process, in which melamine melt is continuously sprayed and cooling medium is continuously removed, treated and (optionally) returned thereafter, the quantity of melamine melt that is directly converted in the cooling medium into suspended solid is principally determined by the net residual solubility of the melamine in the net supplied liquid cooling medium at the prevailing temperature, the quantity of supplied melamine melt and the net quantity of supplied cooling medium. The supplied cooling medium may consist of the sum of separate flows with different compositions. The net quantity of added cooling medium is understood to be the sum of the separate supplied liquid flows of cooling medium minus the (possibly) evaporated quantity of cooling medium in the cooling vessel. The net residual solubility of the melamine is understood to be the quantity of melamine that can still dissolve in the supplied cooling medium at the prevailing temperature in the cooling vessel. If the cooling medium may already contain (recirculated) solid or dissolved melamine, the net residual solubility is lower than the thermodynamic solubility of melamine in the cooling medium at the prevailing temperature in the cooling vessel. If a (recirculated) saturated melamine solution is used as a cooling medium, the net residual solubility can still be larger than zero, if the temperature in the cooling vessel is higher than the temperature of the supplied cooling medium. The solubility of melamine in the liquid cooling medium is generally higher at a higher temperature, if the temperature of the cooling medium is lower than $0.9 * T_{crit}$, where $T_{crit}$ is the critical temperature of the cooling medium expressed in Kelvin.

In a continuous process the fraction of melamine melt that is obtained directly as a solid in the form of suspended melamine particles is defined with the following formula: $100\% * (M - c * K)/M$, where M=the supplied melamine melt flow (unit: kg/s)

K=net supplied cooling medium flow (unit: kg/s)

c=net residual solubility of the melamine in the cooling medium at the prevailing temperature in the cooling vessel (unit: kg melamine per kg of net supplied cooling medium).

This invention is particularly suitable in a continuous process, because then it is easy to set a constant value for c. As a result the product characteristics can be controlled more easily.

In one embodiment of the method according to the invention the suspension formed is withdrawn from the space in which the crystallisation has taken place by cooling and in a following process step wholly or partially separated into solid melamine and the cooling medium. The recovered cooling medium, after it has been brought again to the temperature desired for the cooling and the $CO_2$ content, if necessary, has been brought again to the desired value, is preferably returned to the cooling vessel. The cooling medium may also contain, in addition to dissolved melamine, still solid melamine. For recovering the solid melamine particles from the suspension techniques known per se can be applied. Examples thereof are gravity-induced sedimentation, separation in a hydrocyclone, centrifuging and filtering, in all cases if desired followed by a drying stage and if desired preceded by a thickening step.

In another embodiment the temperature of the suspension can first be raised or lowered before the melamine particles are separated. The particle size can be influenced further with this extra step.

The method according to the invention is very suitable to be included in a continuous process for manufacturing melamine and obtaining it in a pure form. The method may be carried out in a separate vessel in which the cooling medium is present and in which spraying of the melamine melt takes place at the top and the suspension of melamine particles in the cooling medium is removed, at the bottom. The method may however also be carried out in a compartment of a larger reactor in which several successive steps of the process are carried out. The method according to the invention may be incorporated in the known processes for the production of melamine in a high-pressure process. Such processes have been described for example in Ullmann's Encyclopedia of Industrial Chemistry, Vol. A 16, fifth ed., P. 177-179, Nitrogen No. 228, July-August 1997, P. 43-51, Nitrogen & Methanol, No. 233, May-June 1998, P. 35-40 and WO 02/100839. In all the processes described therein a melamine melt is formed which, if necessary after a pretreatment for the removal of $CO_2$ or an excess of ammonia or another pretreatment of the melt described therein as favourable or desired, can be converted into melamine particles with favourable properties by means of the method according to the invention.

The invention claimed is:

1. A method for crystallising a melamine melt to form melamine particles with a $D_{90}$ of at most 2 mm comprising cooling in a liquid cooling medium a melamine melt to below the crystallisation temperature of the melamine, forming a suspension of melamine particles in the cooling medium by spraying the melamine melt with at most 10 wt % of $CO_2$ relative to the sprayed quantity of melamine melt in a space in which a layer of the liquid cooling medium is present that has a temperature below the crystallisation temperature of the melamine and under cooling conditions at which at least 50 wt % of the sprayed melamine melt directly turns into suspended melamine particles.

2. The method according to claim 1, wherein with the liquid cooling medium is comprised of at least 90 wt % of liquid ammonia.

3. The method according to claim 1, further comprising controlling the temperature of the cooling medium by evaporation of the coolant.

4. The method according to claim 1, further comprising cooling the temperature of the cooling medium by bringing it in contact with an environment with a lower temperature than the temperature of the cooling medium.

5. The method according to claim 1, comprising spraying the melamine melt together with a gas as a two-phase flow.

6. The method according to claim 1, comprising spraying the melamine melt directly in the cooling medium.

7. The method according to claim 1, further comprising separating the melamine particles from the suspension of crystallised melamine in the cooling medium.

8. A method for manufacturing melamine from urea in a high-pressure process, comprising reacting urea to form melamine in a reactor at a pressure between 4 and 25 MPa and a temperature between 330 and 430°C., separating the formed reactor product into a flow that consists principally of liquid melamine and a flow that consists principally of $CO_2$, $NH_3$ and melamine vapour, performing crystallisation by cooling the liquid melamine, using a cooling medium, to below the crystallisation temperature at which solid melamine is formed and separating the solid melamine, and wherein crystallisation is practiced by the method according to claim 1.

9. The method according to claim 8, wherein the high-pressure process is a continuous process.

* * * * *